(12) United States Patent
Wozencroft

(10) Patent No.: US 11,583,296 B2
(45) Date of Patent: Feb. 21, 2023

(54) GUIDE FOR POSITIONING A RESURFACING HEAD IMPLANT

(71) Applicant: Embody Orthopaedic Limited, London (GB)

(72) Inventor: Robert Michael Wozencroft, Central London (GB)

(73) Assignee: Embody Orthopaedic Limited, London (GB)

( * ) Notice: Subject to any disclaimer, the term of this patent is extended or adjusted under 35 U.S.C. 154(b) by 241 days.

(21) Appl. No.: 16/771,610

(22) PCT Filed: Dec. 12, 2018

(86) PCT No.: PCT/EP2018/084633
§ 371 (c)(1),
(2) Date: Jun. 10, 2020

(87) PCT Pub. No.: WO2019/115648
PCT Pub. Date: Jun. 20, 2019

(65) Prior Publication Data
US 2020/0297360 A1    Sep. 24, 2020

(30) Foreign Application Priority Data

Dec. 13, 2017 (GB) .................................... 1720804

(51) Int. Cl.
*A61B 17/17* (2006.01)
*A61B 17/16* (2006.01)
(Continued)

(52) U.S. Cl.
CPC ........ *A61B 17/175* (2013.01); *A61B 17/1668* (2013.01); *A61B 17/8866* (2013.01); *A61B 2017/00862* (2013.01)

(58) Field of Classification Search
CPC .............. A61B 17/175; A61B 17/1721; A61B 17/1753; A61B 17/1767; A61B 17/1775;
(Continued)

(56) References Cited

U.S. PATENT DOCUMENTS

2008/0215057 A1* 9/2008 Willi .................... A61B 17/175
606/88
2009/0240253 A1* 9/2009 Murray ................ A61B 17/175
606/102
(Continued)

FOREIGN PATENT DOCUMENTS

EP    1477120 A1    11/2004
EP    1588668 A1    10/2005
(Continued)

OTHER PUBLICATIONS

"International Application Serial No. PCT/EP2018/084633, International Search Report dated Apr. 2, 2019", 5 pgs.
(Continued)

*Primary Examiner* — Amy R Sipp
(74) *Attorney, Agent, or Firm* — Schwegman Lundberg & Woessner, P.A.

(57) ABSTRACT

A femoral head guide clamp can include jaws and two opposing arms that extend from the jaws. The jaws can include an aperture shaped such that the jaws have a closed position in which the aperture fits around a femoral neck of a patient but is too small to accept a femoral head of a patient, and an open position in which the aperture is expanded such that it is large enough to allow the femoral head to pass through. The arms can include a proximal section in which the arms are substantially parallel in a side-by-side arrangement, and a distal section in which the
(Continued)

Figure 1:
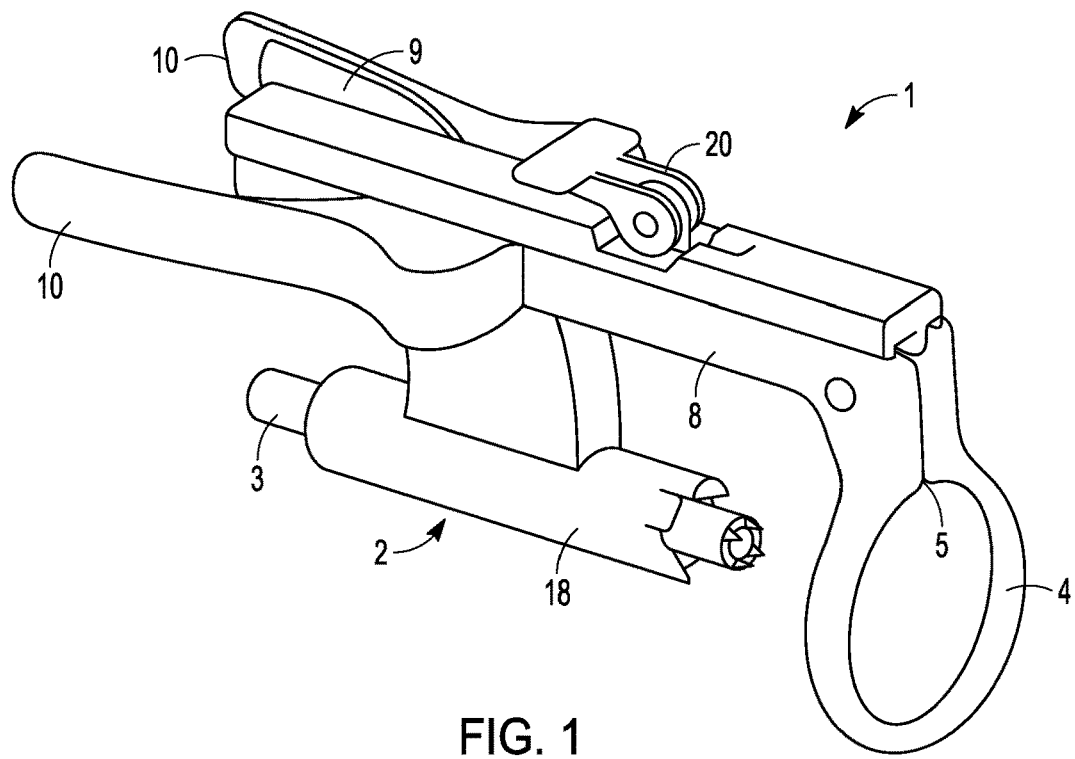

arms extend away from each other such that moving the two distal sections towards each other moves the jaws towards the open position.

20 Claims, 8 Drawing Sheets

(51) Int. Cl.
*A61B 17/88* (2006.01)
*A61B 17/00* (2006.01)

(58) Field of Classification Search
CPC . A61B 17/1717; A61B 17/1739; A61B 17/17; A61B 17/1668; A61B 17/8866; A61B 17/90
See application file for complete search history.

(56) References Cited

U.S. PATENT DOCUMENTS

| | | | |
|---|---|---|---|
| 2009/0254093 A1* | 10/2009 | White | A61B 17/175 606/88 |
| 2010/0114101 A1 | 5/2010 | Crofford | |
| 2013/0066321 A1* | 3/2013 | Mannss | A61B 17/1778 606/88 |

FOREIGN PATENT DOCUMENTS

| | | |
|---|---|---|
| EP | 1772106 A1 | 4/2007 |
| EP | 3490470 A1 | 6/2019 |
| WO | WO-03055400 A1 | 7/2003 |
| WO | WO-2005112805 A2 | 12/2005 |
| WO | WO-2006112805 A1 | 10/2006 |
| WO | WO-2010148103 A1 | 12/2010 |
| WO | WO-2018025021 A1 | 2/2018 |
| WO | WO-2019115648 A1 | 6/2019 |

OTHER PUBLICATIONS

"International Application Serial No. PCT/EP2018/084633, Written Opinion dated Apr. 2, 2019", 7 pgs.

"United Kingdom Application Serial No. 1720804.2, Combined Search and Examination Report dated May 16, 2018", 8 pgs.

"United Kingdom Application Serial No. 1720804.2, Response filed Dec. 2012 Combined Search and Examination Report dated May 16, 2018", 14 pgs.

"United Kingdom Application Serial No. 1720804.2, Subsequent Examiners Report dated Jan. 3, 2020", 5 pgs.

"United Kingdom Application Serial No. 1720804.2, Subsequent Examiners Report dated Jan. 3, 2020", 15 pgs.

"United Kingdom Application Serial No. 1720804.2, Subsequent Examiners Report dated Apr. 2, 2020", 6 pgs.

"European Application Serial No. 18826232.3, Response to Communication pursuant to Rules 161(1) and 162 EPC filed Feb. 2, 2021", 15 pgs.

"International Application Serial No. PCT/EP2018/084633, International Preliminary Report on Patentability dated Jun. 25, 2020", 9 pgs.

"United Kingdom Application Serial No. 1720804.2, Office Action dated Oct. 14, 2020", 2 pgs.

"United Kingdom Application Serial No. 1720804.2, Response filed Aug. 3, 2020 to Subsequent Examiners Report dated Apr. 2, 2020", 18 pgs.

* cited by examiner

GUIDE FOR POSITIONING A RESURFACING HEAD IMPLANT

This application is a U.S. National Stage Application under 35 U.S.C. 371 from International Application Serial No. PCT/EP2018/084633, filed on Dec. 12, 2018, and published as WO 2019/115648 A1 on Jun. 20, 2019, which claims priority to United Kingdom Application No. 1720804.2, filed on Dec. 13, 2017, the benefit of priority of each of which is claimed hereby, and each of which are incorporated by reference herein in its entirety.

BACKGROUND

During a hip resurfacing operation, the head of a patient's femur is normally retained and capped with a head implant with a spherical bearing of a similar size to the natural joint. The bone socket in the pelvis is reamed to approximately a hemispherical shape and a thin walled cup implant is fitted to completely reline the hip joint with an artificial bearing. In order to regain natural range of motion and to ensure the bearing functions well over a long period of time, it is very important to position both the head and cup implants correctly relative to the natural bone and soft tissue structures. This is particularly challenging in a diseased hip where the head of the femur is often misshapen and the acetabular socket may have migrated slightly out of position. This can be misleading when it comes to positioning the implant components. Furthermore, the surgeon has limited access and visibility during the operation, so it can be difficult to visualise anatomical landmarks and to judge the orientation of the bones.

When the surgeon positions a resurfacing head implant on the femur bone the following factors are generally considered:

1. Femoral head/neck size: The choice of head implant size should be approximately the same as the natural head size, whilst at the same time there must be enough bone available on the head to support the implant fully and it is vital that the cutters used to prepare the head do not encroach into the femoral neck (known as notching) as it weakens the bone and can cause femoral neck fracture postoperatively.
2. Varus/valgus angle: This is the angle between the femur shaft axis and the head implant axis and should be in the range 135-145 degrees so that the load is transferred through the implant without putting undue stress on the bone.
3. Version angle: This is the forward tilt angle of the femoral neck relative to the frontal anatomical plane. It is unique for each patient and usually within the range 15-25 degrees. The surgeon will try to place the head axis according to the natural femoral neck version angle for a specific patient.

Patient specific guides are sometimes used in joint replacement operations to help position implants. They are defined and constructed preoperatively based on three-dimensional digital images of the patient's joints. The digital images of the patient's joint can be reconstructed from medical scans of the patient using commercially available CAD (Computer Aided Design) and/or other specific planning software. The surgeon or skilled technician interacts with the software to place the implant in the desired positions relative to the patient's scanned bones. A patient matched guide is then defined and constructed using rapid prototyping techniques such as additive manufacture. These guides are devised to fit exactly with a patients exposed bone surfaces intraoperatively so that the implants can be directed exactly to their planned positions. An advantage of a patient specific head guide for the resurfacing head is that multifactorial variables listed (1-3) above are all resolved simultaneously according to a pre-operative plan as the guide fits exactly into a distinct position on the femur bone.

STATEMENT OF INVENTION

The present invention is a guide for positioning a resurfacing head implant into the appropriate position and orientation on the femur bone. In the context of the invention, the word "proximal" is used to refer to a part of the guide which is closer to the patient's femur shaft during use, and the word "distal" is used to refer to a part of the guide which is further away from the patient's femur shaft during use.

In a first aspect, the present invention relates to a femoral head guide clamp comprising:
 (a) jaws comprising an aperture which is shaped such that
  (i) the jaws have a closed position in which the aperture fits around a femoral neck of a patient but is too small to accept a femoral head of a patient, and (ii) the jaws are movable from the closed position to an open position in which the aperture is expanded such that it is large enough to allow the femoral head to pass through, and
 (b) two opposing arms that extend from the jaws and which have a proximal section in which the arms are substantially parallel in a side-by-side arrangement, and a distal section in which the arms extend away from each other such that moving the two distal sections towards each other moves the jaws towards the open position.

In particular, the jaws may include a lockable member for securing the jaws in the closed position.

More particularly, the aperture may be formed by a ring comprising a discontinuity, the ring being openable at the discontinuity when the jaws are moved towards the open position in order to allow the femoral head to pass through the ring. Even more particularly, the jaws may extend away from the ring in a direction which is substantially coplanar with the ring, and then connect to the arms which extend distally in a direction which, in use, is towards a user of the femoral head guide clamp.

In particular, the distal section of at least one of the two opposing arms may comprise protrusions which are shaped to be received by corresponding depressions on the opposing arm when the two distal sections are moved towards each other to move the jaws towards the open position.

In particular, the femoral head guide clamp may additionally comprise a guide for a drill or cutter. More particularly, the guide for a drill or cutter may be removable. Even more particularly, the removable guide may be slidably attachable to the two opposing arms of the femoral head guide clamp. More particularly, the removable guide may be slidably attachable to the proximal sections of the arms. In particular, the two opposing arms may each comprise an elongate rail extending along each arm and which are shaped to mate with two corresponding elongate recesses on the removable guide. More particularly, the removable guide may comprise a lockable member for securing the removable guide to the femoral head guide clamp. Even more particularly, the removable guide may comprise a lockable member for securing the removable guide to the femoral head guide clamp, the lockable member being able to press the elongate rails against a wall of each of the elongate recesses in order to secure the removable guide to the femoral head guide clamp.

In particular, one or both of the femoral head guide clamp and the removable guide may be a patient specific instrument. More particularly, the jaws may be provided with one or more neck protrusions which are shaped such that the jaws are only moveable to the closed position when around a femoral neck of a specific patient and when the femoral head guide clamp is in a predefined orientation relative to that patient's femur. Even more particularly, the neck protrusions may be shaped as substantially flat ribs. More particularly, the aperture may be formed by a ring comprising a discontinuity and the neck protrusions are provided on the ring. Even more particularly, the neck protrusions may extend in one or more of the following directions: above a plane of the ring, below a plane of the ring, towards a centre of the ring, and away from a centre of the ring.

More particularly, the guide for a drill or cutter may comprise one or more head protrusions which, in use, extend towards a femoral head of a specific patient and which are shaped to conform to the surface of the femoral head when the jaws are closed around a femoral neck of the patient. Even more particularly, the head protrusions may be shaped as substantially flat ribs which additionally extend axially away from the removable guide.

In particular, one or both of the femoral head guide clamp and the removable guide may be formed from a resilient material. More particularly, the resilient material may be a polyamide.

In a second aspect, the present invention relates to method of clamping a femoral head guide clamp as described above to a femur, the method comprising the steps of:
(a) opening the jaws of the femoral head guide clamp,
(b) passing the femoral head through the aperture, and
(c) closing the jaws of the femoral head guide clamp.

In particular, the jaws may include a lockable member for securing the jaws in the closed position and the method may comprise the additional step, after step (c), of:
(d) locking the jaws in the closed position.

More particularly, the method may additionally include the step of attaching a guide for a drill or cutter to the femoral head guide clamp. Even more particularly, the two opposing arms may each comprise an elongate rail extending along each arm and which are shaped to mate with two corresponding elongate recesses on the removable guide, and the step of attaching comprising sliding the removable guide onto the elongate rails. In particular, the attaching step may be carried out after step (c) or after step (d) and may comprise contacting a femoral head with the removable guide.

In a third aspect, the present invention relates to a computer-readable medium having computer-executable instructions adapted to cause a 3D printer to print a femoral head guide clamp and/or a removable guide as described above.

DETAILED DESCRIPTION

A purpose of the guide is to position a drilled hole in the femur bone which defines the orientation and position of a resurfacing head implant. Two embodiments of the guide are described herein, a generic guide which comes in a range of sizes and may be used for any patient, and a patient specific guide which is tailored to fit a specific patient's anatomy. Both embodiments are preferably manufactured in plastic (for example polyamide) using an additive manufacturing process. The skilled person is aware of several types of additive manufacturing processes, for example selective laser sintering (SLS) or stereolithography (SLA). Alternatively, these parts could be moulded in plastic, for example by injection moulding or cold curing casting resin. Alternatively, they could be manufactured in plastic by any other means.

The guide may be made up of two parts, a femoral head guide clamp and a removable drill guide. The head guide clamp includes a circular ring, which, in use is positioned around the neck of the femur bone. The ring includes opening jaws, where the ring joins to two opposing arms. These arms extend approximately perpendicular to the plane of the ring. The arms have a proximal section where they are parallel in a side-by-side arrangement and a distal section where the arms form handles which move away from one another.

The head guide clamp is manufactured from a resilient material (for example polyamide) and can, for example, be flexed open in one of two ways to enable it to be positioned around the neck of the femur bone. A first method is to prise the handles apart by holding one handle in each hand. An opening movement allows the ring to expand open and become large enough for it to pass over the femoral head. When the opening grip is relaxed, the ring closes around the femoral neck. A second method is to squeeze the distal handle section of the opposing arms together which, due to the shape of the arms including a fulcrum position approximately halfway along (at the intersection of the proximal section and distal section), causes the arms at the proximal end to gape apart and the ring to expand open large enough for it to pass over the femoral head. This second method is convenient for the surgeon because it can be done with one hand.

The drill guide may include a cylindrical boss with an aperture for guiding a drill, an elongated section for connecting it to the head guide clamp and a cam locking lever. When assembled the drill guide may be slidably connected to the proximal section of the head guide clamp. The cam locking lever can allow the drill guide to be locked in a variety of proximal distal positions on the head guide clamp. In use, the drill guide can be moved to a position where the proximal section of the cylindrical boss is as close as possible and preferably in contact with the femoral head. Furthermore, this locking mechanism provides a means for clamping the guide securely between the femoral head and femoral neck.

Preferably a drill tube with a spiked end is inserted into the aperture of the drill guide. The spiked end slides down to contact the femoral head and the spikes can embed into the bone slightly (preferable the drill tube is manufactured in metal such as stainless steel). Then a drill (for example 5 mm in diameter) may be passed through the drill tube and a hole is drilled into the femur bone corresponding to the central longitudinal axis of the resurfacing head implant. The spiked end can ensure that the drill enters the bone without deviating off line.

In the patient specific version of the guide, additional features may be included to make the head guide clamp and drill guide fit a specific patient's femur bone. On the head guide clamp the ring can include protrusions shaped to engage with the bone surface on the patient's femoral neck in several positions, thus providing an exact fit of the guide in a predetermined orientation relative to the patient's femur. Furthermore, on the drill guide, protrusions may be included at the proximal end of the cylindrical boss. These protrusions can be shaped to engage with the surfaces of the patient's femoral head in several positions, thus further enhancing the exact fit of the guide in a predetermined orientation relative to the patient's femur. These opposing features may also provide clamping means between the femoral head and neck.

In an alternative embodiment, the removable drill guide may incorporate a larger diameter cylindrical boss with a large aperture and removable inner collar. The inner collar can be used to guide a small diameter drill (for example a 5 mm drill) into the femur bone but when the inner sleeve is removed, a larger counterbore cutter (for example a diameter 30 mm cutter) may be introduced and guided by the large aperture in the cylindrical boss. Furthermore, the distal end of the cylindrical boss can provide an end stop for the large counter bore cutter. Therefore, provided the patient specific protrusions are in contact with the femoral head surface, the depth of counterbore can be guided to a predetermined depth relative to the patient's femur bone. The counterbore surface coincides with the internal end face of the resurfacing head implant, so that the proximal distal position of the resurfacing head implant may be precisely controlled by the guide. In this case both the proximal distal axis and proximal distal position may be controlled by the guide.

Figure 2:
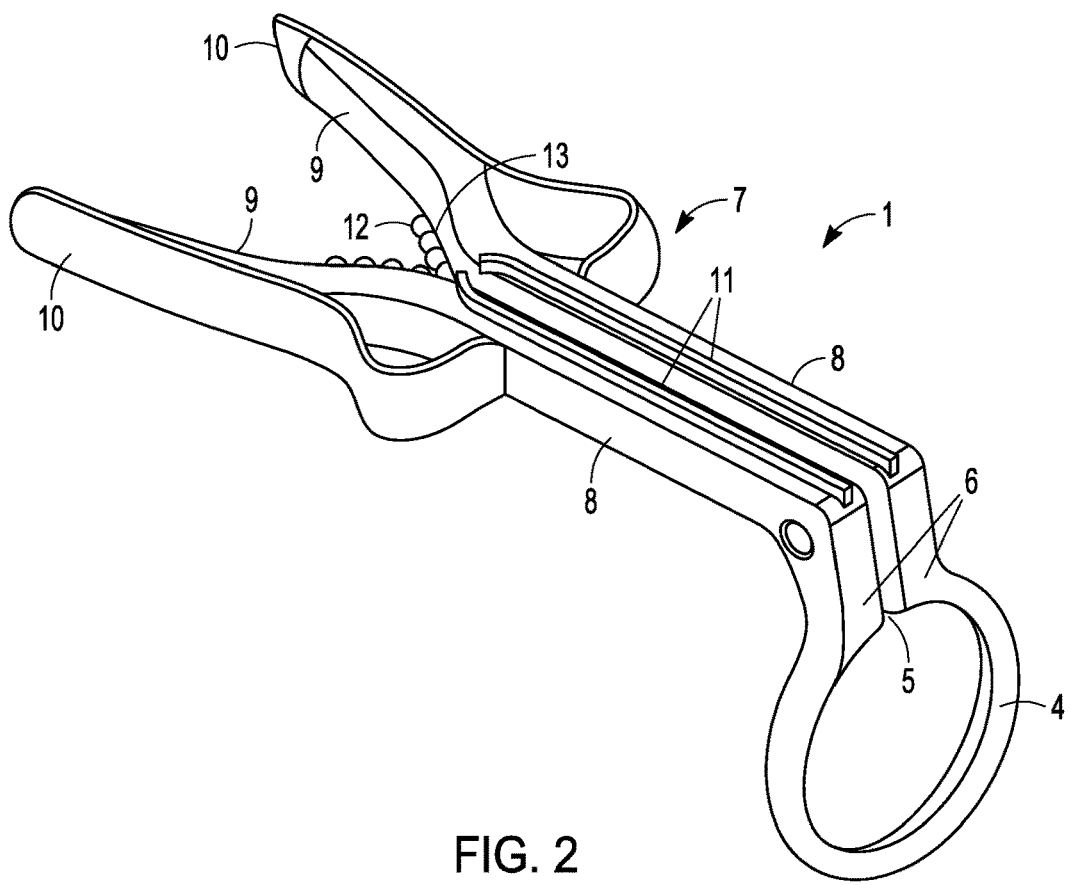
Figure 3:
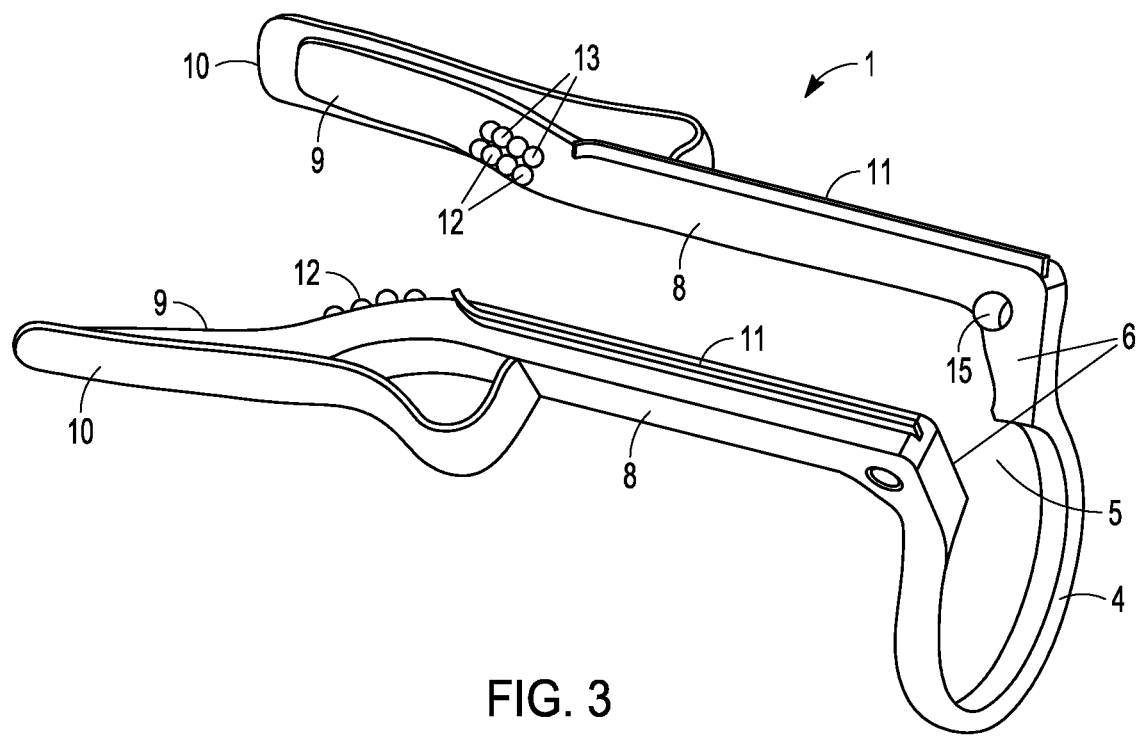
Figure 4:
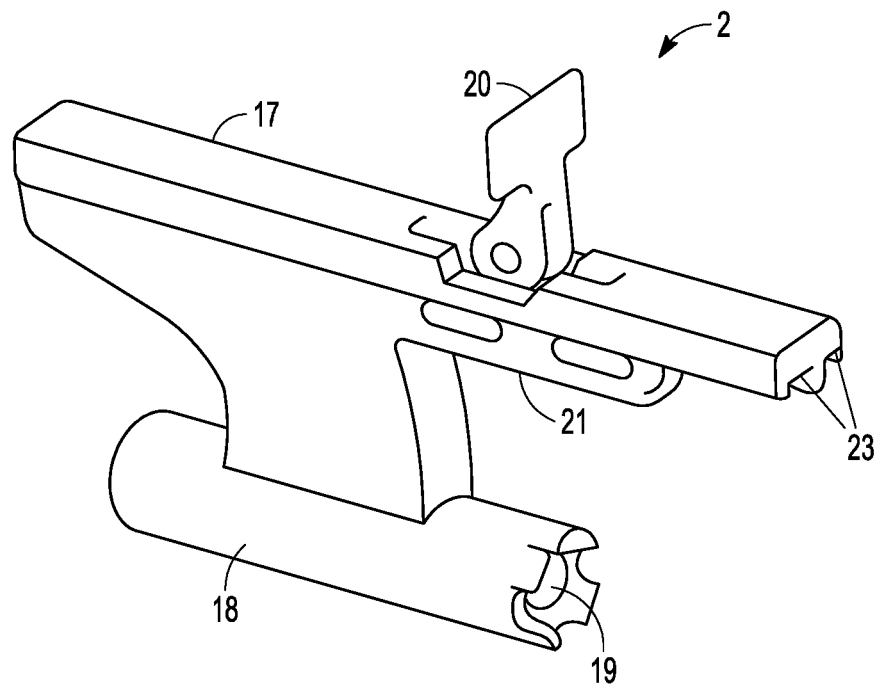
Figure 5:
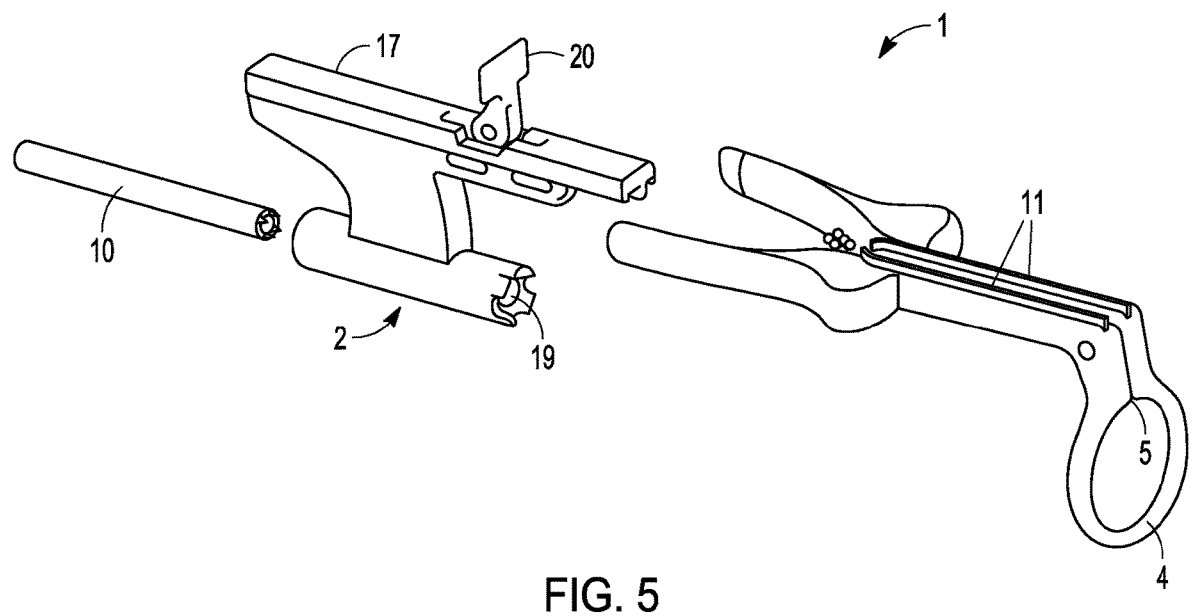
Figure 6:
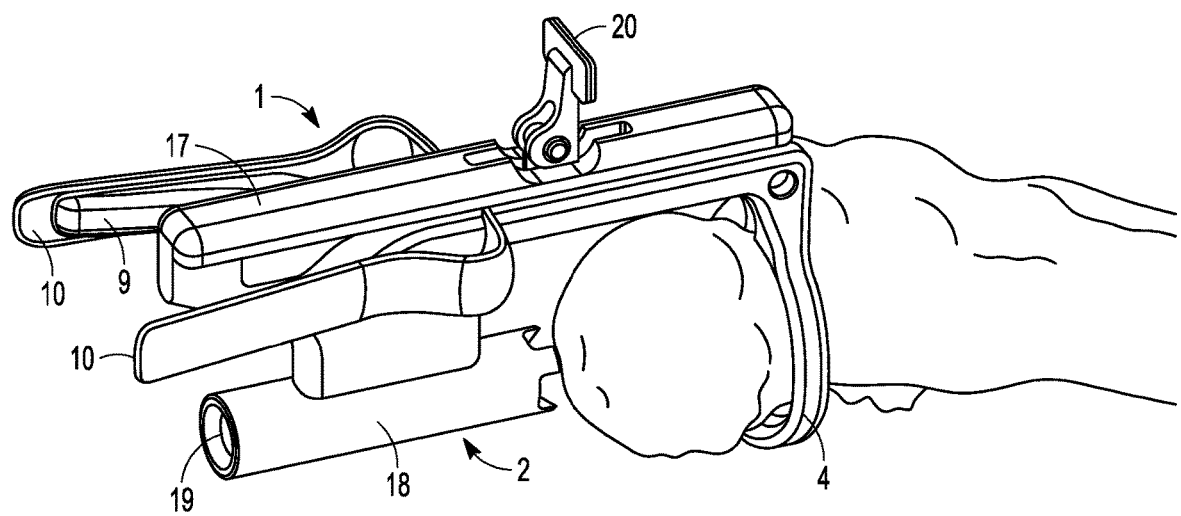
Figure 7:
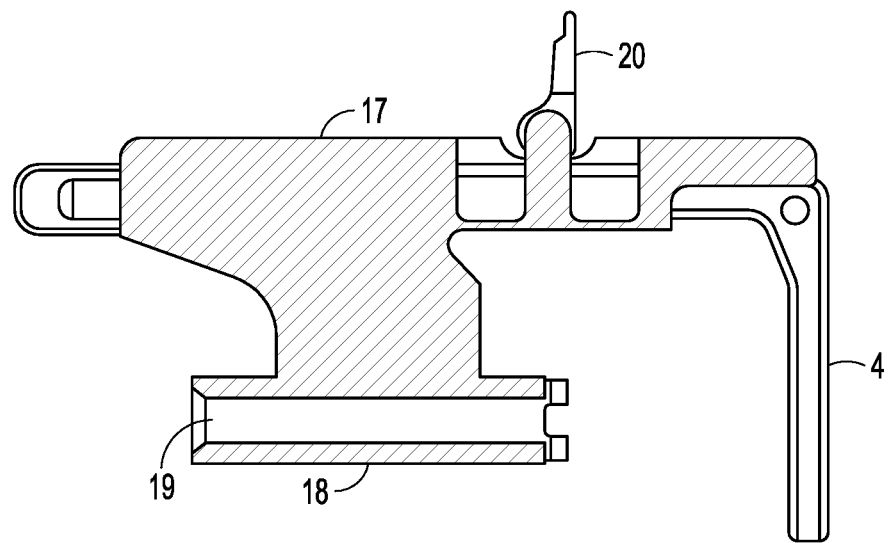
Figure 8:
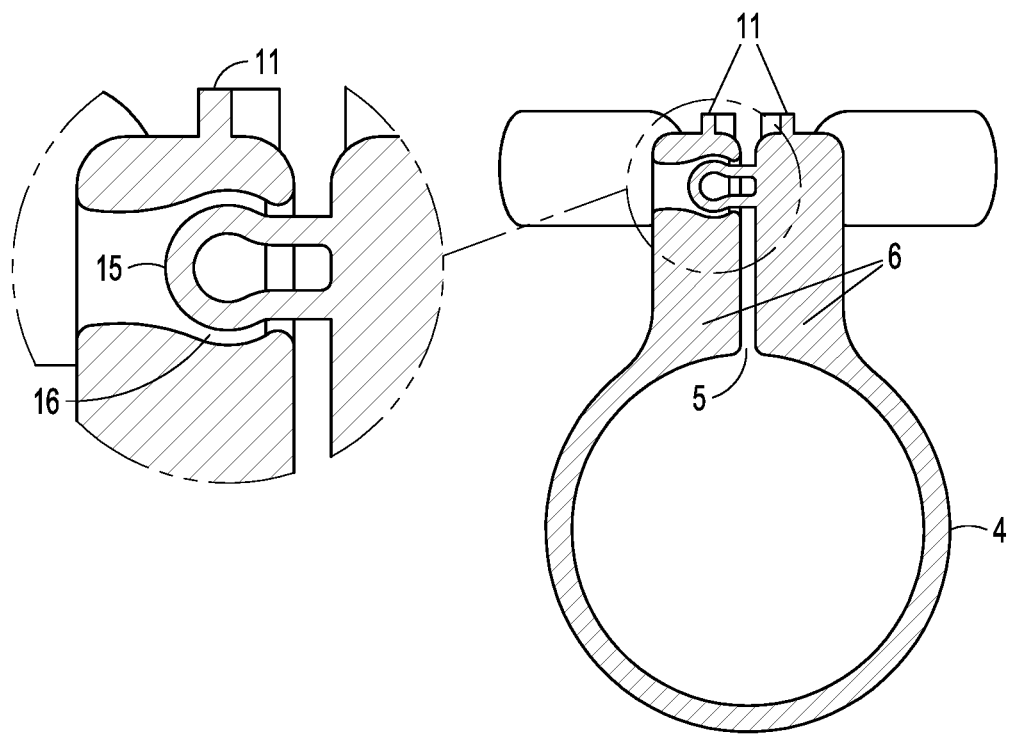
Figure 9:
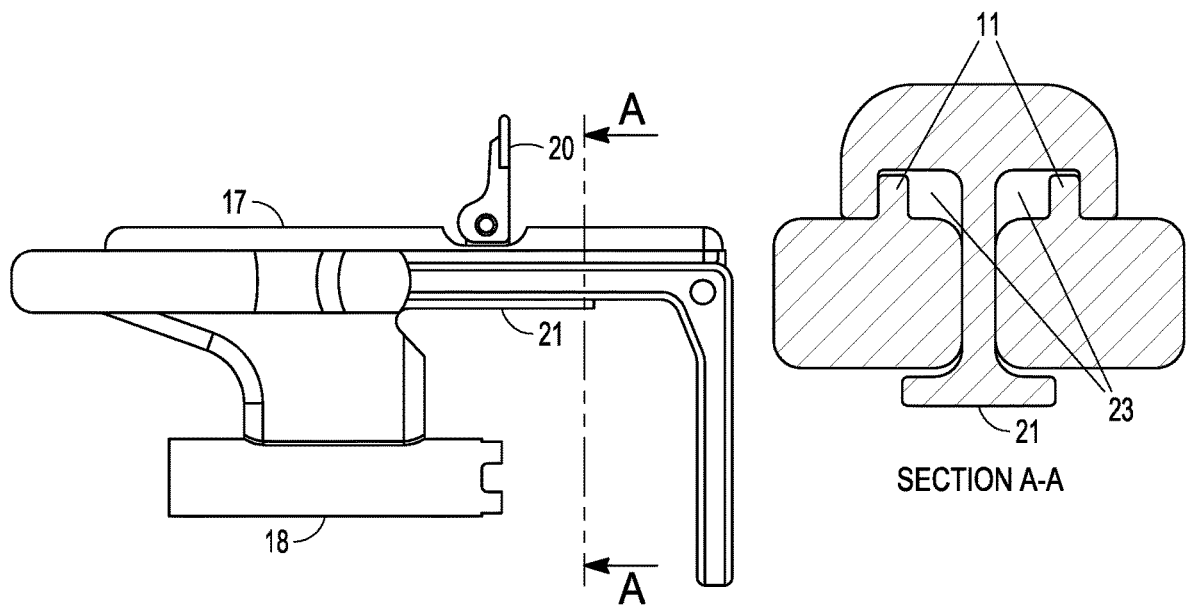
Figure 10:
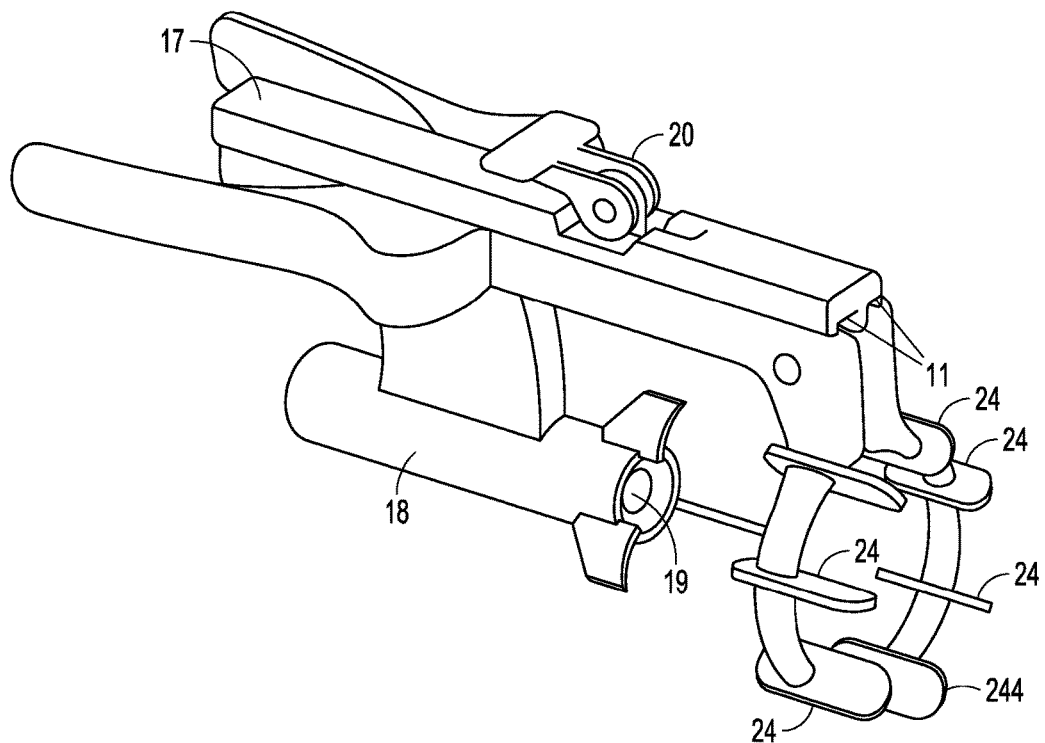
Figure 11:
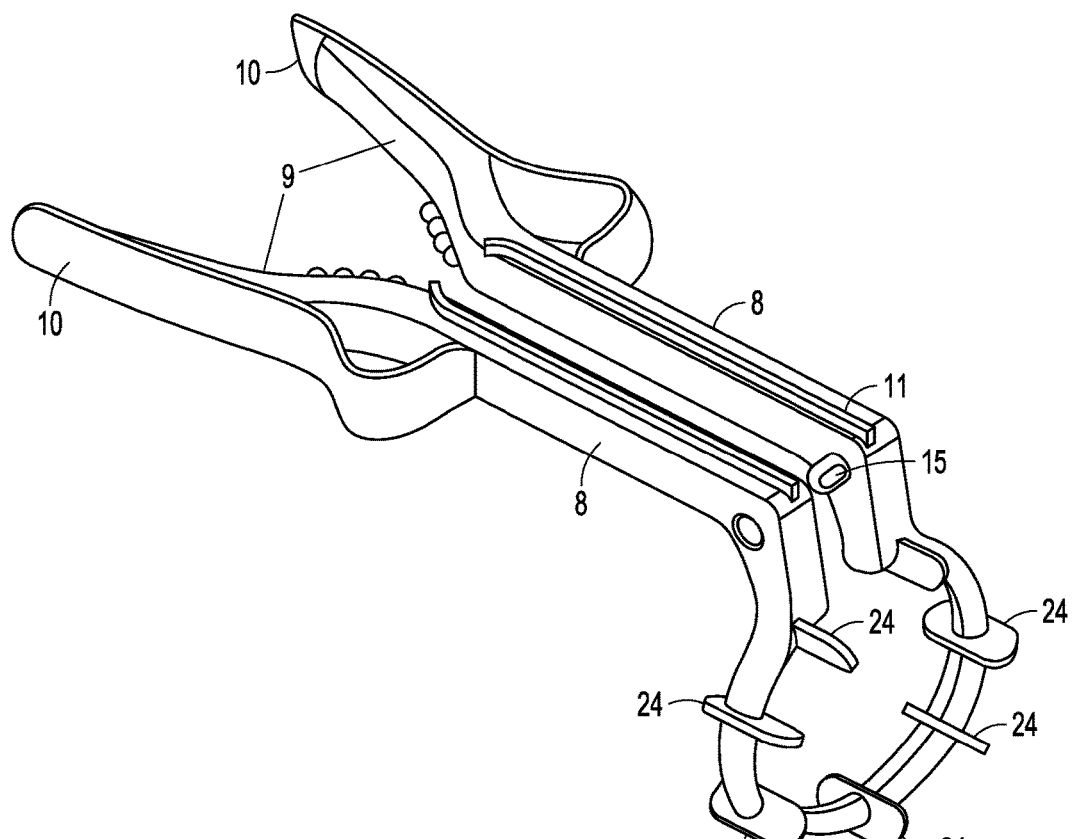
Figure 12:
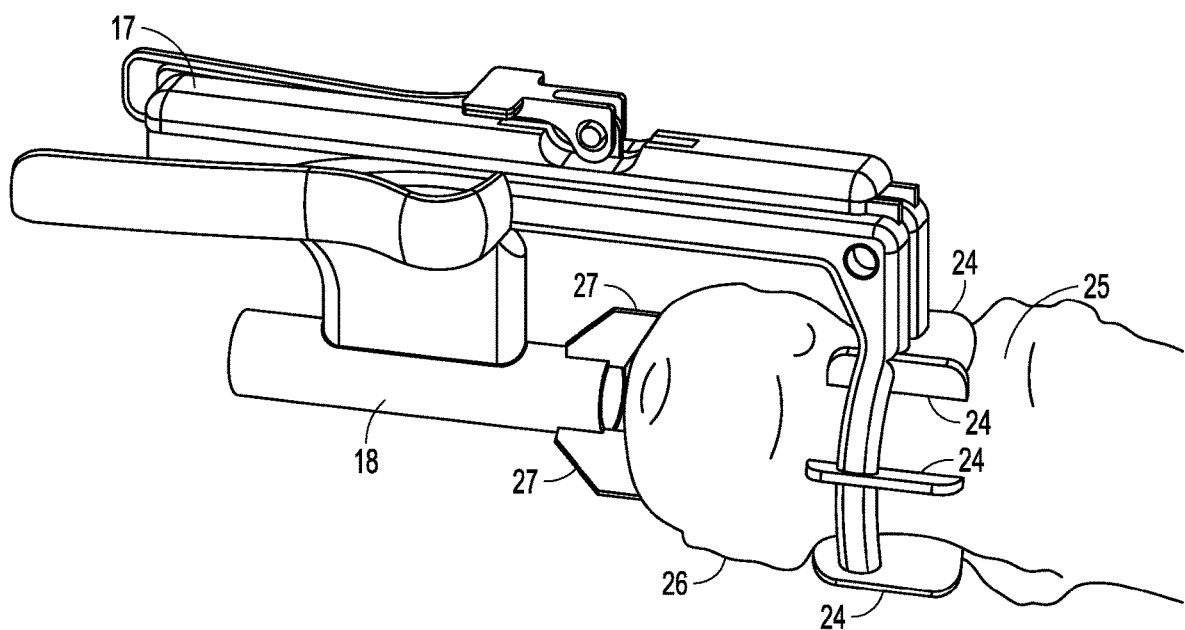
Figure 13:
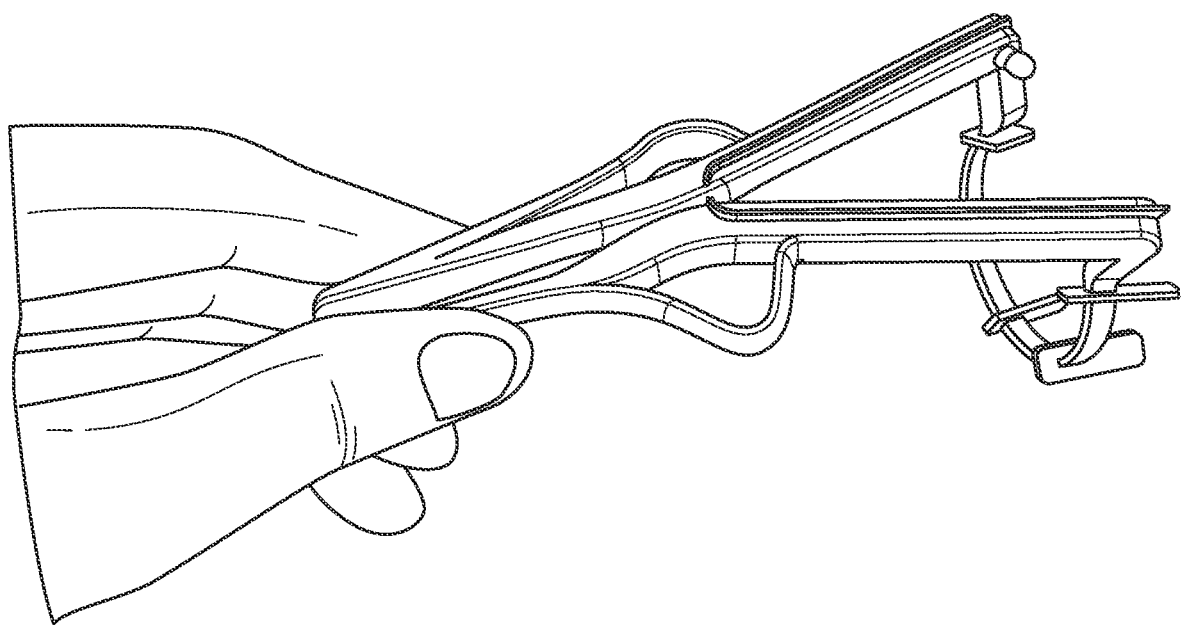
Figure 14:
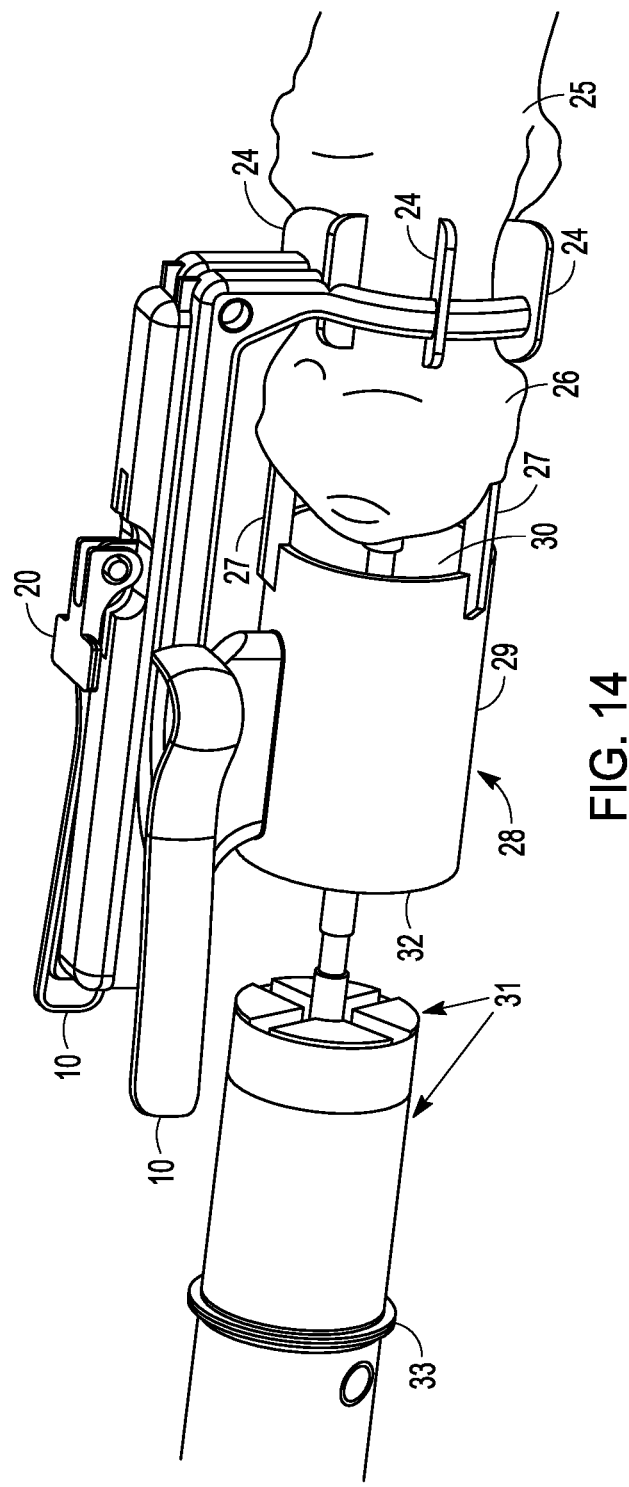

Examples of the invention will now be described by referencing the accompanying drawings, which are not intended to limit the scope of the invention claimed, in which:

FIG. 1 shows the assembled head guide according to one embodiment of the invention, FIG. 2 shows the head guide clamp part of the head guide of FIG. 1 in isolation and in the closed position, FIG. 3 shows the head guide clamp of FIG. 2 in an opened position, FIG. 4 shows the drill guide part of head guide of FIG. 1 in isolation, FIG. 5 is an exploded view of the head guide of FIG. 1, FIG. 6 is the head guide of FIG. 1 assembled in position on a femur bone, FIG. 7 is a cross sectioned view of the drill guide of FIG. 4, FIG. 8 is a view of the head guide clamp of FIG. 2, cross sectioned through the ring, jaws and retaining feature, FIG. 9 is a view of the head guide of FIG. 1, cross sectioned at position A-A, FIG. 10 shows an alternative patient specific version of the head guide, FIG. 11 shows the head guide clamp part of the head guide of FIG. 10 in isolation and in a slightly opened position, FIG. 12 is the head guide of FIG. 10 assembled in position on a femur bone, FIG. 13 shows the head guide clamp of FIG. 11, in an opened position, and FIG. 14 shows an alternative embodiment of a patient specific drill guide.

A generic version of the head guide is shown in FIGS. 1-9. This version comes in a range of sizes, one for each size of resurfacing head implant (for example 10 sizes). A patient specific version of the head guide is shown in FIGS. 10-13 which is manufactured to fit a specific patient's anatomy. An alternative embodiment of a patient specific drill guide is shown in FIG. 14.

In FIGS. 1-5 it can be seen that the head guide comprises a head guide clamp [1], removable drill guide [2] and optionally a spiked tube [3]. The head guide clamp [1] comprises a circular ring [4] with discontinuity [5] and two jaws [6] extending away from the discontinuity [5]. Extending from the jaws are two opposing arms [7], each arm comprises a proximal section [8] where the arms are substantially parallel and distal section [9] where the arms extend away from one another forming handles [10]. The proximal sections of the arms [9] each incorporate an elongated rail [11]. The distal section of the arms incorporates protrusions [12] which are shaped to receive corresponding depressions [13] on the opposing arm when the arms are moved towards each other in a similar way to that shown in FIG. 13 in relation to the patient specific version. In FIG. 8, a retaining feature is shown comprising a spherical stud [15] on one arm and an aperture [16] on the opposing arm, this feature temporarily retains the opposing arms in the closed position.

The removable drill guide [2] comprises body [17] and a cylindrical boss [18] with aperture [19]. The body incorporates a cam locking lever [20]. In FIGS. 4 and 7 the cam locking lever [20] is shown in the unlocked position. When the locking lever [20] is rotated through 90 degrees to the lock position (as shown in FIG. 10 in relation to the patient specific version), inferior flange [21] of the body [17] is pulled upwards (ie towards locking lever [20]) to clamp the drill guide [2] in a certain proximal distal position when assembled on the head guide clamp [1]. In FIG. 9 (Section A-A) the connection between head guide clamp and drill guide is shown, consisting of elongated rails [11] on the head guide clamp and elongated recesses [23] on the drill guide [2]. Sliding movement occurs between the head guide clamp [1] and drill guide [2] in a proximal distal direction and this movement is locked when the cam locking lever [20] is in the locked position.

A patient specific version of the head guide is shown in FIGS. 10-13 which differs from the generic version in that it includes the addition of protrusions on both head guide clamp and drill guide. On the head guide clamp protrusions [24] extend from the circular ring [4] to fit a specific patient's femoral neck bone surfaces, so that when positioned around the femoral neck [25], the head guide clamp will only close successfully when in a predefined orientation relative to the patient's femur. On the drill guide, protrusions [27] extend from the proximal end of the cylindrical boss [18], also to fit the femoral head [26] in a predefined orientation. In FIG. 12, it is apparent how the sliding adjustment in the guide and the ability to lock the drill guide [2] relative to the head guide clamp [1] enables both sets of protrusions [24 & 27] to be in contact with the femoral head [26] and neck [25] simultaneously, forming a stable platform for drilling into the femoral head neck.

An alternative embodiment of the removable drill guide is shown in FIG. 14. In this embodiment the removable drill guide [28] incorporates a larger diameter cylindrical boss [29] with a large aperture [30] and removable inner collar [not shown]. The inner collar is for guiding the small diameter drill (for example a 5 mm drill) into the femur bone but when the inner sleeve is removed, a larger counterbore cutter [31] (for example a diameter 35 mm cutter) is introduced and guided by the large aperture [30] in the cylindrical boss. Furthermore, the distal end of the cylindrical boss [32] provides an end stop for a flange [33] on the large counter bore cutter [31]. Therefore, provided the patient specific protrusions [27] on the removable drill guide [28] are in contact with the femoral head surface [26], the depth of counterbore is guided to a predetermined depth relative to the patient's femur bone. The counterbore surface coincides with the internal end face of the resurfacing head implant [not shown] so that the proximal distal position of the resurfacing head implant is precisely controlled by the guide. In this case both the proximal distal axis and proximal distal position are controlled by the guide.

The invention claimed is:

1. A femoral head guide clamp comprising:
   jaws;
   an aperture shaped such that the jaws have a closed position in which the aperture fits around a femoral neck of a patient but is too small to accept a femoral head of a patient, and the jaws are movable from the closed position to an open position in which the aperture is expanded such that it is large enough to allow the femoral head to pass through; and
   two opposing arms that extend from the jaws in a direction approximately perpendicular to the plane in which the jaws move and which have a proximal section in which the arms are substantially parallel in a side-by-side arrangement, and a distal section in which the arms extend away from each other such that moving the two distal sections towards each other moves the jaws towards the open position.

2. The femoral head guide clamp as claimed in claim 1, wherein the jaws include a retaining feature for securing the jaws in the closed position.

3. The femoral head guide clamp as claimed in claim 1, wherein the aperture is formed by a ring comprising a discontinuity, the ring being openable at the discontinuity when the jaws are moved towards the open position in order to allow the femoral ead to pass through the ring.

4. The femoral head guide clamp as claimed in claim 3, wherein the jaws extend away from the ring in a direction which is substantially coplanar with the ring, and then connect to the arms which extend distally in a direction which, in use, is towards a user of the femoral head guide clamp.

5. The femoral head guide clamp as claimed in claim 1, wherein the distal section of at least one of the two opposing arms comprises protrusions which are shaped to be received by corresponding depressions on the opposing arm when the two distal sections are moved towards each other to move the jaws towards the open position.

6. A guide clamp system comprising:
   a femoral head guide clamp comprising:
      jaws;
      an aperture shaped such that the jaws have a closed position in which the aperture fits around a femoral neck of a patient but is too small to accept a femoral head of a patient, and the jaws are movable from the closed position to an open position in which the aperture is expanded such that it is large enough to allow the femoral head to pass through; and
      two opposing arms that extend from the jaws in a direction approximately perpendicular to the plane in which the jaws move and which have a proximal section in which the arms are substantially parallel in a side-by-side arrangement, and a distal section in which the arms extend away from each other such that moving the two distal sections towards each other moves the jaws towards the open position; and
   a guide for a drill or cutter.

7. The guide clamp system as claimed in claim 6, wherein the guide for a drill or cutter is removable.

8. The guide clamp system as claimed in claim 7, wherein the removable guide is slidably attachable to the two opposing arms of the femoral head guide clamp.

9. The guide clamp system as claimed in claim 8, wherein the removable guide is slidably attachable to the proximal sections of the arms.

10. The guide clamp system as claimed in claim 9, wherein the two opposing arms each comprise an elongate rail extending along each arm and which are shaped to mate with two corresponding elongate recesses on the removable guide.

11. The guide clamp system as claimed in claim 10, wherein the removable guide comprises a cam locking lever for securing the removable guide to the femoral head guide clamp.

12. The guide clamp system as claimed in claim 10, wherein the removable guide comprises a cam locking lever for securing the removable guide to the femoral head guide clamp, the cam locking lever being able to press the elongate rails against a wall of each of the elongate recesses in order to secure the removable guide to the femoral head guide clamp.

13. The guide clamp system as claimed in claim 7, wherein one or both of the femoral head guide clamp and the removable guide is a patient specific instrument.

14. The guide clamp system as claimed in claim 13, wherein the femoral head guide clamp is provided with one or more neck protrusions which are shaped such that the jaws are only moveable to the closed position when around a femoral neck of a specific patient and when the femoral head guide clamp is in a predefined orientation relative to that patient's femur.

15. The guide clamp system as claimed in claim 14, wherein the neck protrusions are shaped as substantially flat ribs.

16. The guide clamp system as claimed in claim 15, wherein the aperture is formed by a ring comprising a discontinuity and the neck protrusions are provided on the ring.

17. The guide clamp system as claimed in claim 16, wherein the neck protrusions extend in one or more of the following directions: above a plane of the ring, below a plane of the ring, towards a center of the ring, and away from a center of the ring.

18. A guide clamp system comprising:
   a femoral head guide clamp comprising:
      jaws;
      an aperture which is shaped such that the jaws have a closed position in which the aperture fits around a femoral neck of a patient but is too small to accept a femoral head of a patient, and the jaws are movable from the closed position to an open position in which the aperture is expanded such that it is large enough to allow the femoral head to pass through; and
      two opposing arms that extend from the jaws in a direction approximately perpendicular to the plane in which the jaws move and which have a proximal section in which the arms are substantially parallel in a side-by-side arrangement, and a distal section in which the arms extend away from each other such that moving the two distal sections towards each other moves the jaws towards the open position; and
   a removable guide for a drill or cutter, the removable guide including one or more head protrusions which, in use; extend towards a femoral head of a specific patient and which are shaped to conform to a surface of the femoral head when the jaws are closed around the femoral neck of the patient.

19. The femoral head guide clamp as claimed in claim 18, wherein the head protrusions are shaped as substantially flat ribs which additionally extend axially away from the removable guide.

20. The femoral head guide clamp as claimed in claim 18, wherein one or both of the femoral head guide clamp and the removable guide are formed from a resilient material.

* * * * *